(12) United States Patent
Robbins et al.

(10) Patent No.: US 10,489,023 B2
(45) Date of Patent: Nov. 26, 2019

(54) OPERATING ROOM CHECKLIST SYSTEM

(71) Applicant: LiveData, Inc., Cambridge, MA (US)

(72) Inventors: Jeffrey Robbins, Cambridge, MA (US); Gabriel Noah Schaffer, Cleveland Heights, OH (US); Brett J. Cohen, Cleveland Heights, OH (US); Arvind Goyal, Sudbury, MA (US)

(73) Assignee: LiveData, Inc., Cambridge, MA (US)

( * ) Notice: Subject to any disclaimer, the term of this patent is extended or adjusted under 35 U.S.C. 154(b) by 240 days.

(21) Appl. No.: 14/872,273

(22) Filed: Oct. 1, 2015

(65) Prior Publication Data

US 2016/0018963 A1 Jan. 21, 2016

Related U.S. Application Data

(62) Division of application No. 13/536,333, filed on Jun. 28, 2012.

(51) Int. Cl.
*G06F 17/20* (2006.01)
*G06F 3/0484* (2013.01)
*G16H 40/20* (2018.01)
*G06F 3/0482* (2013.01)
*H04L 29/08* (2006.01)

(52) U.S. Cl.
CPC .......... *G06F 3/0484* (2013.01); *G06F 3/0482* (2013.01); *G16H 40/20* (2018.01); *H04L 67/025* (2013.01)

(58) Field of Classification Search
CPC .............................................. G06F 19/30–366
See application file for complete search history.

(56) References Cited

U.S. PATENT DOCUMENTS

| 2003/0204411 A1* | 10/2003 | Beyersdorf ........... G06F 19/327 705/2 |
| 2004/0040086 A1 | 3/2004 | Eisenberg |
| 2004/0044546 A1* | 3/2004 | Moore ................. G06F 19/325 705/2 |
| 2004/0064342 A1 | 4/2004 | Browne et al. |

(Continued)

FOREIGN PATENT DOCUMENTS

| JP | 2006-323620 A | 11/2006 |
| KR | 10-09-0032349 A1 | 4/2009 |

OTHER PUBLICATIONS

Extended European Search Report for European Application No. 13808787.9 dated Feb. 24, 2016.

(Continued)

*Primary Examiner* — Keith D Bloomquist
(74) *Attorney, Agent, or Firm* — Wolf, Greenfield & Sacks, P.C.

(57) ABSTRACT

Techniques for generating and providing a checklist, and for providing updates to a checklist based on event data. In some aspects, a checklist is provided to a terminal device by receiving a notification of a trigger event, which is used, at least in part, to obtain a checklist template and to generate a checklist from the checklist template, which is then provided to the terminal device. In some aspects, a server device provides a checklist to a terminal device, the checklist comprising a sequence of prompts, each prompt indicating one or more actions, and the server device provides an update to the checklist based on received event data.

25 Claims, 10 Drawing Sheets

(56) References Cited

U.S. PATENT DOCUMENTS

| | | |
|---|---|---|
| 2005/0015276 A1 | 1/2005 | Sullivan et al. |
| 2007/0078678 A1 | 4/2007 | DiSilvestro et al. |
| 2007/0136097 A1* | 6/2007 | Demers ............. G06Q 10/0635 |
| | | 705/2 |
| 2007/0136218 A1* | 6/2007 | Bauer ................... G06F 19/345 |
| | | 706/12 |
| 2009/0089081 A1 | 4/2009 | Haddad |
| 2010/0305970 A1 | 12/2010 | McLaren et al. |
| 2010/0305971 A1* | 12/2010 | McLaren ............. G06Q 10/06 |
| | | 705/3 |
| 2010/0324933 A1 | 12/2010 | Giap |
| 2011/0137680 A1 | 6/2011 | Sweeney |
| 2011/0145017 A1* | 6/2011 | Lee ....................... G06Q 10/10 |
| | | 705/3 |
| 2012/0101841 A1* | 4/2012 | Kobayashi ............ G06Q 10/06 |
| | | 705/2 |
| 2012/0239420 A1* | 9/2012 | Stapelfeldt ............ G06Q 10/10 |
| | | 705/2 |
| 2012/0323597 A1* | 12/2012 | Woolford ............. G06F 19/321 |
| | | 705/2 |
| 2013/0285947 A1* | 10/2013 | Hunter .................. G09G 5/003 |
| | | 345/173 |
| 2014/0006943 A1 | 1/2014 | Robbins et al. |

OTHER PUBLICATIONS

Bardram et al., A Context-aware Patient Safety System for the Operating Room. Proceedings of the 10$^{th}$ International Conference on Ubiquitous Computing. UBICOMP. 2008;272-81.

International Search Report and Written Opinion for International Application No. PCT/US2013/048481 dated Oct. 18, 2013.

* cited by examiner

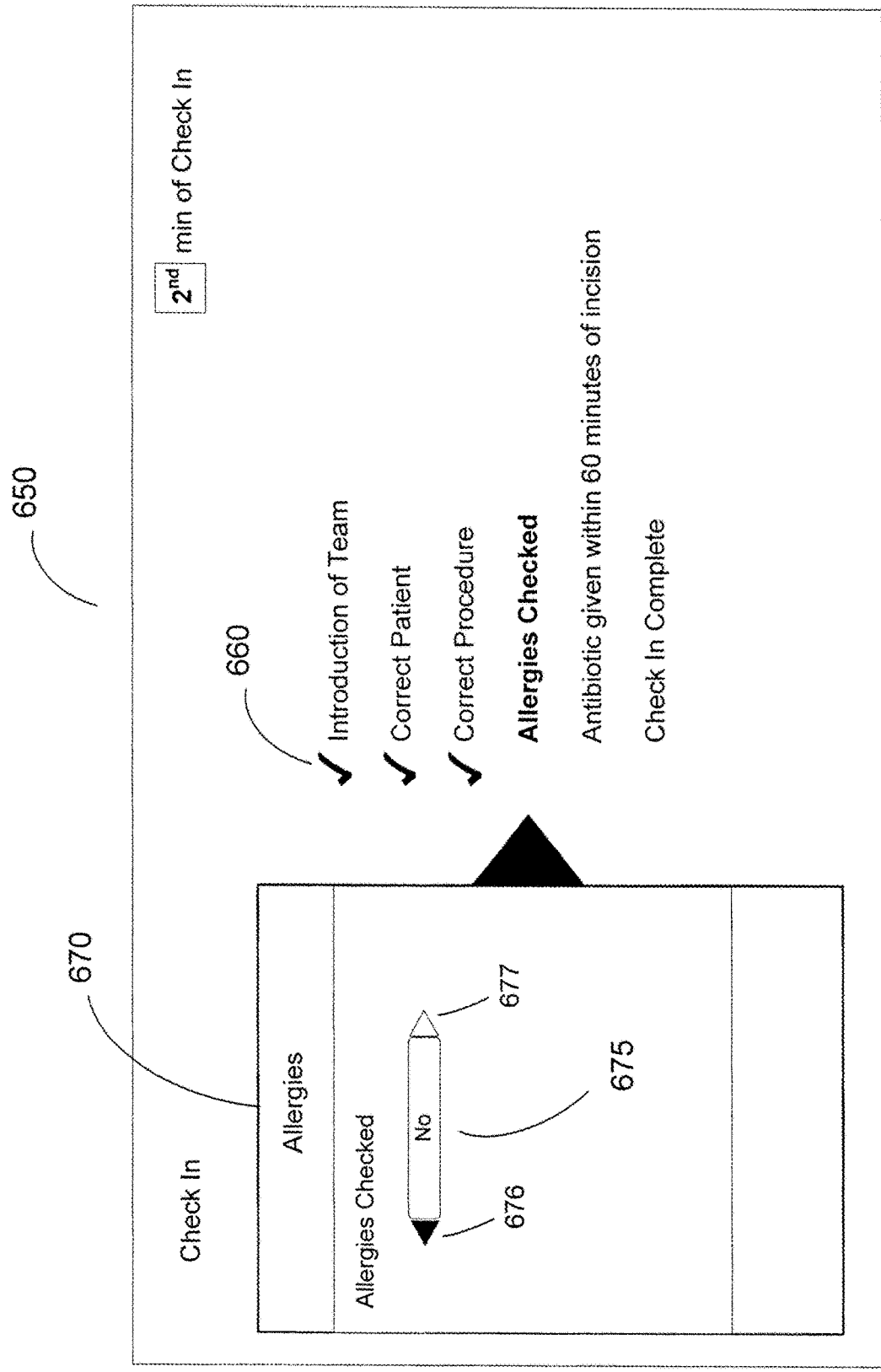

FIG. 6C

4th min of Check In

✓ Introduction of Team
✓ Correct Patient
✓ Correct Procedure
✓ Allergies Checked
Antibiotic given within 60 minutes of incision
Check In Complete

— 680

Check In | Antibiotics
Antibiotic Administered
**Cefazolin 1 g
@ 07:40**

OK — 695

690

OPERATING ROOM CHECKLIST SYSTEM

CROSS-REFERENCE TO RELATED APPLICATION

This Application is a divisional of and claims the benefit under 35 U.S.C. § 120 of U.S. patent application Ser. No. 13/536,333 entitled "OPERATING ROOM CHECKLIST SYSTEM," filed Jun. 28, 2012, which is herein incorporated by reference in its entirety.

FIELD OF THE INVENTION

This invention relates to the field of medical safety systems and methods. More particularly, it relates to enhancing the safety of surgical procedures and reducing the risk of errors in operating rooms.

BACKGROUND

Hospital operating rooms are both the site of life-saving and life-enhancing surgical procedures, as well as being the site of many preventable human errors committed in the course of patient treatment. These errors have many causes, including miscommunications among the involved personnel, inattention to important safety protocols, lack of proper information such as patient-specific information, and so forth. Various studies report the observed causes of some of these errors, and efforts to reduce the error rate. Still, significant errors occur at greater than desired rates.

One way that some hospitals seek to reduce the rate and severity of such errors, and to manage their risk of exposure to lawsuits for negligence (medical malpractice), is to require operating room personnel (e.g., nurses and/or technicians and/or physicians) to utilize checklists to remind them of actions they should take and to record that the suggested or required actions are completed. However, experience has shown that such use of checklists is far from perfect. Sometimes, an incorrect checklist is used. Other times, a checklist is not followed and actions are not taken at the intended times, but someone fills out the checklist, or a portion of the checklist, after-the-fact. This makes the answers unreliable, at least to a degree, and certainly not useful to establish an evidentiary record that correct procedures were followed. If an intended step was omitted or performed out of order, and the surgical outcome is influenced, there is no way, absent accurate records, to evaluate the situation. Moreover, individual surgeons or surgical departments often prefer protocols that differ from the "usual" procedure. Operating room personnel may make innocent mistakes because of lack of familiarity with the surgeon's standard practices that deviate from the hospital's standard practices or another department's standard practices.

Moreover, so-called best practices, and corresponding checklist content, may vary according to a patient's particulars, the latest information in medical literature or decisions by supervisory medical personnel, to give but a few reasons. Extra steps in the process are needed for the user to first confirm that the proposed checklist is, in fact, the most recent applicable checklist, and the correctness of that confirmation depends on the inquiry which is made and how much is known about the patient when the inquiry is made. For example, if there are two available checklists, one for a diabetic patient and one for a non-diabetic patient, the wrong checklist can be selected if the user has incorrect information about the patient's status with respect to diabetes. To avoid use of the wrong checklist, a comprehensive checklist covering both (and other) options may be provided. In order to cover the variations in procedure that a given patient's particulars may require (e.g., due to the patient being diabetic, allergic, obese, elderly, a child, pregnant, etc.), however, a single all-encompassing paper checklist can become lengthy and unwieldy. Including a lot of alternatives and requiring the user to make a lot of decisions about which sections to use and which sections to skip not only takes time and generates stress, but also leads to errors.

Thus, use of conventional paper checklists is not without problems and shortcomings. For example, conventional paper checklists are typically limited by the methods by which a user may indicate that a checklist item has been completed, they are limited by the ease of updating the checklist and distributing updated checklists to ensure that information contained within the checklist remains current and appropriate for the situation, and their reliability and accuracy as a data collection tool are only so good as the users' adherence to proper procedure. That is, they lack credibility as audit tools. Since it is impractical in many cases to distribute paper checklists customized to the patient, doctor, etc., comprehensive omnibus checklists are more often than not the norm, and their lack of tailored content leads to usage errors.

Furthermore, information that a user may need to determine a correct response to a conventional checklist item may not be known to the user even though a co-worker knows the information. With a paper checklist system, it may be difficult for the user to obtain this information, or to parse out portions of the checklist to other users/members of the surgical team, thus making the user's responses to checklist items potentially less accurate and less reliable.

This does not even take into account that data may be "forged" on a paper checklist. For example, a nurse, physician or technician responsible for the checklist may indicate (e.g., at the end of a surgery) that certain steps were completed that never, in fact, were executed. For a checklist to be used during a surgery time-out (when the surgery is paused to perform checks, etc.), it may be particularly important to ensure the checklist was used correctly, and used at the correct time. Failure to do so may result in an increase of risk to the patient's health and to the hospital's potential liability.

Computerized checklists may provide a way for a user to indicate that a checklist item has been completed in a more convenient manner than with a paper checklist (e.g., by checking (e.g., clicking on) a box using any one of a number of devices). However, conventional computerized checklist systems are typically nearly as limited as paper checklist systems are, in their ability to dynamically provide up-to-date information and assure the desired delivery of services and confirmation of same.

SUMMARY

These and other shortcomings of prior checklist systems are addressed by the systems and methods presented herein.

Some embodiments include a processor-driven method of providing a medical checklist to a terminal device, the method comprising operating one or more processors to execute stored program instructions causing the one or more processors to receive a notification that a trigger event has occurred, the notification comprising an event identifier, a case identifier and one or more event data items, obtain a checklist template from a checklist template repository based on at least one of: the event identifier, the case identifier and at least one of the one or more event data items, create a medical checklist comprising case information based on the case identifier, the checklist template and at least one of the one or more event data items, and display the medical checklist on a terminal device.

Some embodiments provide a system for providing a medical checklist to a terminal device, the system comprising a server device configured to receive a notification that a trigger event has occurred, the notification comprising an event identifier, a case identifier and one or more event data items, obtain a checklist template from a checklist template repository based on the event identifier and the one or more event data items, create a medical checklist comprising case information based on the case identifier, the checklist template and the one or more event data items, and provide the medical checklist to a terminal device.

Some embodiments provide a system for providing and administering medical checklists, the system comprising a plurality of terminal devices, each terminal device configured to display a medical checklist comprising a sequence of prompts, each prompt indicating one or more actions, and receive input from a user in response to a prompt of the sequence of prompts, the input signifying that an action of the one or more actions indicated by the prompt is being performed, and a server device configured to provide medical checklists to the plurality of terminal devices, receive event data indicating one or more medical activities, update one or more of the medical checklists on a terminal device based on the received event data.

Some embodiments provide a processor-driven method of providing and administering medical checklists, the method comprising at a server device, providing a medical checklist to a terminal device, the medical checklist comprising a sequence of prompts, each prompt indicating one or more actions, at the terminal device, displaying the medical checklist, and at the server device, receiving event data indicating one or more medical activities and providing an update of one or more of the medical checklists to the terminal device based on the received event data.

Some embodiments provide an operating room including a computer-driven medical checklist presentation and administration system comprising one or more sensors configured to provide a notification of a trigger event to a server; and one or more terminal devices, each terminal device configured to receive a medical checklist from the server comprising a sequence of prompts, each prompt indicating one or more actions, display the medical checklist, and receive input from a user in response to a prompt of the sequence of prompts, the input signifying that an action of the one or more actions indicated by the prompt has been performed.

BRIEF DESCRIPTION OF DRAWINGS

The accompanying drawings are not intended to be drawn to scale. In the drawings, for purposes of clarity, not every component may be labeled in every drawing. In the drawings:

FIG. 6B illustrates a second step of an exemplary checklist, in accordance with some embodiments;

FIG. 6C illustrates a third step of an exemplary checklist, in accordance with some embodiments;

DETAILED DESCRIPTION

Figure 1:
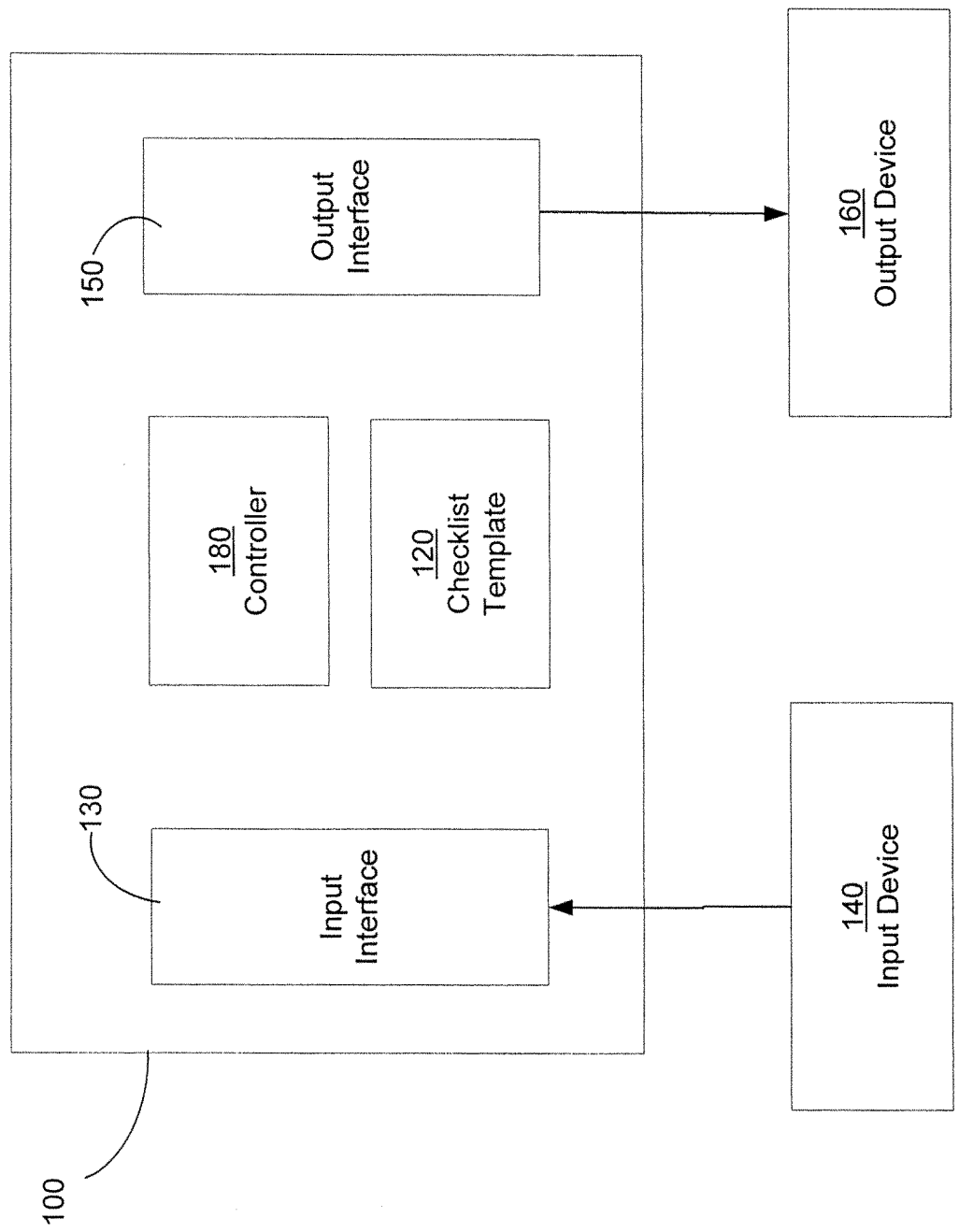
FIG. 1 illustrates a system suitable for providing an electronic, interactive checklist according to some embodiments.

As discussed above, conventional checklist systems are typically limited in the ways by which relevant information may be kept up to date. Such information can be of many types. For example, it may include the collection of available checklists, their content, instructions or criteria for using a particular checklist, information contained within the checklist, or even information that may be used by the checklist user in using the checklist. Conventional checklist systems are also limited in the way information is gathered to populate a checklist and how that information is safeguarded from fraud, or tampering and alteration. An improved checklist system may be provided by ensuring, via a computerized information processing system, that active, current data and current checklist content are provided to each person and device (each a "user") that may access a checklist, whether for input (and storage) of information and/or for display. Furthermore, in such a system a checklist may be generated automatically in response to a trigger event, which makes the use of such an automatically provided checklist faster and more convenient for a user. It also further facilitates use of a common checklist by multiple users.

A checklist generally refers to a sequence of pre-configured prompts, each prompt indicating one or more actions. The system, after delivering a prompt, may or may not wait for information to be input in response to the prompt, which may be via user interaction with the checklist (system), before proceeding to the next prompt in the sequence of prompts.

While it should be appreciated that the techniques and systems discussed herein, or at least some aspects of them, individually and in various combinations, will be useful in many contexts, they are particularly useful in medical situations, particularly operating rooms. Thus, according to some embodiments, the checklist is a medical checklist that includes prompts and/or actions that relate to one or more medical activities and this example context will be used to illustrate features and aspects of the invention disclosure.

The checklist system and techniques described herein may provide a reliable and convenient way to provide and/or administer checklists, which may be applied in any suitable situation in which use of a checklist may be desired. Exemplary applications for checklists include a check-in procedure for a hospital operating room ("OR"), an OR preparation procedure, a patient preparation procedure, a debrief for a patient post-surgery, a pre-incision "time-out" prior to surgery, a "time-out" during surgery, as procedure for responding to an event occurring during surgery, etc. "Surgery" may include any manual and/or instrumental technique performed on or to a patient to investigate and/or treat a disease and/or injury, or to help improve bodily function and/or appearance. Cutting of tissue is not necessarily required. While surgery may include, for example, open heart surgery or an organ transplant, it also may include injections such as Botox injection for cosmetic surgery, an angioplasty procedure, an endoscopy procedure, a dental procedure (e.g., tooth filling), physical therapy, etc. It should be appreciated that checklist techniques and systems described herein may be applied to numerous other situations, and the particular example applications are neither exhaustive nor limiting.

As discussed above, an electronic checklist typically includes or provides a sequence of prompts, and each prompt may indicate one or more actions to be taken on information to be supplied/recorded. A checklist may be provided to a device suitable for presenting (displaying) the checklist (from one to many items/prompts at a time). Suitable devices include many types of terminal devices which also may process input from a user. That input may cause the terminal device itself to determine a subsequent prompt or action, and/or may initiate a communication with another device, such as a server, to determine a subsequent prompt or action. A terminal device may obtain a checklist automatically, such as in response to a trigger event. By using information about a trigger event, a use case may be determined and a checklist may be generated based on the use case, and the checklist may be provided to a user. The device to which an automatically generated checklist is provided may, or may not, be the generator of the trigger event that caused the checklist to be generated. In general, the mechanism by which a trigger event is generated and the resulting actions performed by the system as a result of the trigger event are independent, and each may involve distinct or overlapping sets of users and/or devices. Accordingly, a dynamic, event-driven system may be provided in which checklists are generated, provided, and updated based on user interactions and/or dynamically obtained data.

Trigger events facilitate automated checklist generation in addition to automatic updates to checklists Trigger events may be generated by one or more input devices, and the type of trigger event and/or the type of input device may impact how a checklist is generated and/or updated as a result of the trigger event. To use an example in the context of a hospital operating room (OR), consider a patient being prepared for surgery in an OR. That patient may be connected to various physiological monitors and those instruments may provide input to a checklist system. A monitor or the portion of the system receiving input from the monitor may generate a trigger event due to a physiological condition of the patient. Information relating to the physiological monitor itself (e.g., the monitor's serial number), in addition to information captured by the physiological monitor (e.g., the patient's blood pressure, the current date and time, etc.), may be used to generate and/or perform updates to one or more checklists as well as the patient's records. For example, checklist entries may be generated to require administration of medication to lower the patient's blood pressure.

Following below are more detailed descriptions of various concepts related to, and embodiments of, methods and apparatus according to the aspects of present invention. It should be appreciated that various aspects described herein may be implemented in any of numerous ways. Examples of specific implementations are provided herein for illustrative purposes only. In addition, the various aspects described in the embodiments below may be used alone or in any combination that is sensible, and are not limited to the combinations explicitly described herein.

FIG. 1 depicts a schematic view of a system 100 suitable for practicing electronic checklist techniques according to some embodiments. In particular, system 100 is configured to provide a checklist template 120, as a starting point from which one or more patient and/or circumstance-specific checklists may be generated. In some uses, a checklist may be generated from a checklist template 120 in response to a trigger event, such as may be indicated by input device 140. For example, input device 140 may include a sensor and processing capabilities to provide data from the sensor to input interface 130. Input device 140 may be any one or combination of input devices capable of receiving input, and the type of device may depend on the type of input the particular instance of the system supports. For example, input device 140 may be a sensor, such as a physiological sensor, touch sensor or motion sensor, that allows data to be provided to the system. It should be appreciated that input device 140 may include any type of input component or device, alone or in any combination, that can provide data relating to one or more relevant events, including but not limited to controllers, such as a remote input device or a voice controller, in addition to a microphone, keypad, touch screen, mouse, writing pad, computer, timer, etc., some examples of which are discussed in further detail below.

Data provided by input device 140 may be processed by a programmed processor(s) in input interface 130, for example, to determine whether a checklist is to be generated from checklist template 120 and/or whether a checklist is to be updated via output interface 150. For example, data received by input interface 130 may comprise audio data, and input interface 130 may convert the audio data into text (e.g., via an automated speech recognition system) or into some other form, before the data is used to determine a subsequent action by the system. Input interface 130 may be any one or combination of hardware and/or software that may receive and/or convert and/or analyze data received from input device 140. The logic (i.e., algorithm(s)) implemented in input interface 130 is a matter of produce design and is not restricted by these teachings in any particular way.

A checklist(s) generated from checklist template 120 may be provided, via output interface 150, to output device 160 capable of presenting a checklist to a user. For example, output device 160 may include a display configured to present some or all of a checklist generated from checklist template 120, to a user. Output device 160 may also include other output devices alone or in combination including, but not limited to, a monitor, tablet computer, smart phone, audio speaker, dumb terminal, thin client, etc. some examples of which are discussed in further detail below. According to some embodiments, input device 140 and output device 160 are part of the same apparatus. For example, input device 140 may be a keyboard, and output device 160 may be a display, wherein both the keyboard and display are part of the same thin-client computer system.

Output interface 150 may also provide updates to a checklist that was previously provided to output device 160. The particular output devices that receive an update to a checklist may be one, some, or all of the output devices to which the checklist was previously provided. For example, a particular output device may be targeted to receive an update to a checklist. Such targeting of output devices may be based on processing performed by one or more elements of system 100 and/or on data received from one or more input devices, for example from input device 140.

Checklist template 120 may include information that may be used to generate a specific instance of a checklist. The checklist template may include information indicating how a checklist may be created from the checklist template, such as information from which one or more prompts and/or actions may be generated by system 100. For example, a checklist template may include keywords that may be used in conjunction with data from input device 140, or data generated by input interface 150, to determine whether generating a checklist from checklist template 120 is to be performed, and/or how to use checklist template 120 to create the checklist. Further details of generating a checklist from a checklist template are provided below. It should be appreciated that checklist template 120 may be a combination of software and/or hardware (e.g., program instructions stored on at least one non-transitory, computer readable storage medium that perform, at least in part, the functionality of the checklist template when executed on one or more processors).

System 100 also includes controller 180 to control one or more aspects of the functionality of the system. For example, controller 180 may include one or more processors for executing software (stored in the controller, e.g., in a computer-readable storage medium), firmware or microcode programmed to control and/or perform some functionality of output interface 130 and/or input interface 150 and to process checklist template 120. Controller 180 may include one or more processors, control units, memories (i.e., non-transitory computer-readable storage media, however embodied—e.g., semiconductor, optical, magnetic, etc.), interconnections and/or other hardware or software to allow communication and interaction between the components of system 100. Controller 180 may be formed from any combination of hardware, software and/or firmware to facilitate operation of the system and to process checklist template 120. The subject matter of checklist template 120 may relate to many different situations. The number of checklist templates stored in the system, for its users to select as a basis for a new checklist, is limited only by available storage. For example, available checklist templates might include a surgery sign-in checklist template, a surgery debrief checklist template, a surgical time-out checklist template, or any other suitable type of checklist template.

Figure 2:
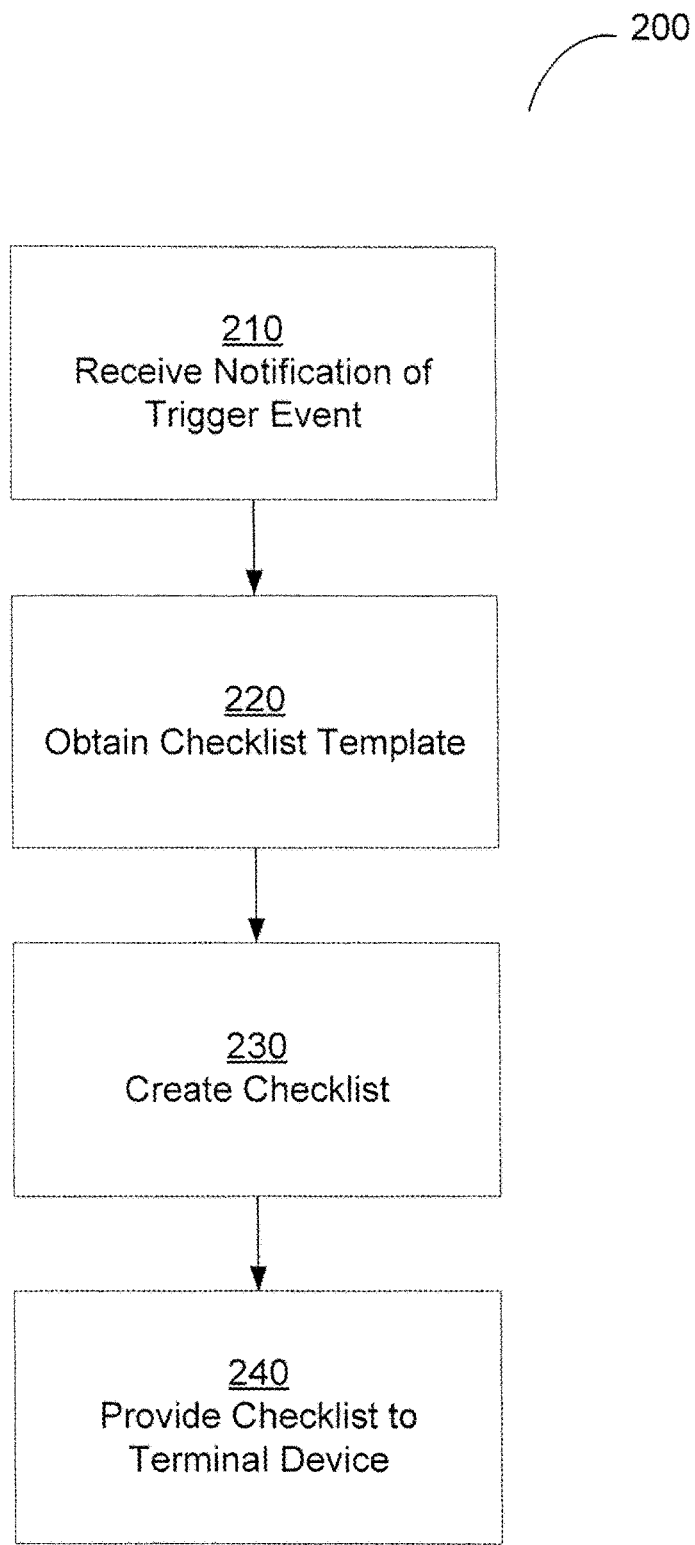
FIG. 2 shows a method of providing an electronic, interactive checklist to a terminal device, according to some embodiments.

FIG. 2 illustrates a method of providing a checklist to a terminal device, in accordance with some embodiments. Method 200 may be performed to provide a checklist in a wide variety of applications that may benefit from such techniques including, but not limited to, surgical procedures, medical patient intake procedures, inpatient care procedures, etc. Method 200 provides a checklist to a terminal device based on a checklist template and guided, at least in part, by information obtained from a trigger event. The trigger event may, but need not be, generated by one or more sensors or controllers, or in response to user data input. By dynamically generating a checklist based on a trigger event, a checklist that is tailored to a specific use case and that contains up-to-date information may be provided, as discussed in further detail below.

In act 210, notification of a trigger event is received. The trigger event may be any event due to which the generation (or modification) of a checklist may be desired. Examples of trigger events include, but are not limited to, a patient entering an operating room, a user providing data to a terminal device, a timer reaching a predetermined date and/or time, an action taken in an OR such as a patient beginning to receive anesthesia, etc. The notification received in act 210 may be any message comprising information on the trigger event, and may be received via hardware and/or software. The notification may include information such as the current date and/or time, and may include an event identifier, which may be a unique identifier associated with the notification.

The notification of a trigger event may be generated via any suitable technique, which may depend on the type of trigger event. For example, the trigger event of a patient entering an operating room may generate a notification of the trigger event in any number of ways, including but not limited to: by a radio frequency identification (RFID) tag worn by the patient being registered by a sensor in the operating room, by a nurse in the operating room entering information indicating the presence of the patent in the operating room, by a physiological monitor known to be in the operating room broadcasting data that indicates the presence of the patient, etc. Each trigger event may result in the generation of notifications by multiple techniques or devices, such as the example techniques or devices described herein. The use of multiple techniques or devices to generate notifications may improve the reliability of data captured by trigger events by providing two or more indications of the same trigger event.

The notification of a trigger event may include one or more event data items, each of which may, or may not, be used to obtain a checklist template and/or to create a checklist or modify an existing checklist which is in use. In some cases, the notification of a trigger event may not result in the generation of a checklist but some or all of the notification may be stored, for example for reporting purposes. Such stored data may be used, for example, to generate reports of how frequently a particular operating room is used for a particular surgery or for any other reporting or analytical purpose. In general, a notification of a trigger event may be stored or logged (e.g., date and time stamped together with a sampling of relevant data values at that time), either in whole or part, using any suitable hardware at any location and for any reason, independently of whether the notification is used to obtain a checklist template and/or to generate or modify a checklist. Some or all of a notification of a trigger event may be stored to be subsequently used when creating a checklist, as will be described in further detail below.

The notification of a trigger event may include a case identifier which identifies a "case" associated with the trigger event. For example, where the trigger event is a patient entering or leaving an operating room, the notification may include a patient identification number or a unique identifier associated with the particular surgery being performed on the patient. However, any identifier that relates to the trigger event and/or the patient may be used as a case identifier. By incorporating multiple items of data, such as a case identifier, an event identifier and/or one or more event data items in the notification, a checklist that is highly customized to the situation may be provided.

In act 220, a checklist template is obtained (retrieved) from storage. As described above, the checklist template may include information that may be used to generate a checklist. Such information may include a sequence of prompts, each prompt indicating one or more actions, and/or other information indicating to the system how a checklist may be created from the checklist template. The checklist template may be obtained based on the notification of a trigger event received in act 210.

The checklist template may include information that may be used to present a checklist generated from the checklist template, at a terminal device. For example, the checklist template may indicate one or more mechanisms by which a prompt or action in a checklist generated from the checklist template may be responded to, such as a list of possible responses (e.g., "YES", "NO", or "N/A"), or as one or more constraints (e.g., the value should be in the range 0 to 120). In the latter case, a constraint may be specified by reference to a particular type of prompt or action, e.g., by specifying that the prompt is querying a patient's systolic blood pressure, which implies a range of numeric constraints on the value (e.g., 50-250), rather than specifying one or more constraint values as in the above example.

As discussed above, the notification of a trigger event may include a case identifier, an event identifier and/or one or more event data items, some or all of which may be used to obtain the checklist template. For example, the checklist template may be obtained based on one or more of: the type of trigger event that caused the notification to be generated (e.g., 'a patient entered a room', 'surgery has been completed', etc.), a case identifier, the name of a patient, an identifier associated with a particular operating room, a description of a procedure associated with the trigger event, the name of a surgeon associated with the trigger event, and/or any other suitable information that relates to the trigger event and/or the notification of the trigger event.

As a further example, the notification of a trigger event may include an event identifier that indicates the trigger event to be a patient being prepped for an appendectomy operation, which may be used to select a checklist template for an appendectomy sign-in. As a yet further example, the notification of a trigger event may include an event identifier that indicates the trigger event to be a patient entering an operating room and may also include an event data item indicating the number of the operating room being used. In this case, the event identifier and the event data item may be used to obtain a checklist template that is customized to that particular operating room (e.g., the checklist template may include information on particular equipment known to be located in—or absent from—the operating room).

The checklist template also may be obtained using information inferred from the notification of a trigger event. For example, the notification of a trigger event may include an event data item that identifies a particular patient, and this event data item may be used to determine that the patient has high blood pressure (e.g., by looking up the patient's medical records). In this case, a checklist template including a prompt for patients with high blood pressure may be obtained based on the information about the patient inferred from the notification of the trigger event. Other cases where a checklist template may be obtained based on patient information and/or even data items include, but are not limited to, when the patient is diabetic, when the patient has a history of heart disease, when the patient is under 18 years old, etc.

Checklist templates may be obtained using the notification of a trigger event and with any suitable technique. Examples of such techniques include, but are not limited to, string or pattern matching of candidate checklist templates with information included in the notification, performing a lookup using some or all of the information in the notification, scoring candidate checklist templates and selecting the checklist template with the highest score, etc.

A checklist template may include one or more attributes that, at least in part, determine whether that particular checklist template is chosen in act 220. One or more attributes may increase the likelihood that the checklist template will be chosen in particular use cases. For example, a checklist template may include an attribute that indicates an association with heart surgery, which may increase the likelihood that the checklist template will be chosen in response to a trigger event of a patient having a heart bypass operation.

One or more attributes included in a checklist template may decrease the likelihood that the checklist template will be chosen in particular use cases. For example, a checklist template may include an attribute that indicates it is not to be used in association with a particular operating room, which may decrease (or reduce to zero) the likelihood that the checklist template will be chosen in response to a trigger event generated from that operating room. One or more attributes included in a checklist template may neither increase nor decrease the likelihood that the checklist template will be chosen in particular use cases. For example, a checklist template may include an attribute that indicates that the checklist template may be used with a patient of any age. The age of the patient may thereby have no effect on the likelihood that the checklist template is chosen.

In some embodiments, checklist templates are chosen, at least in part, based on a comparison of the attributes in all available checklist templates and the contents of a notification of a trigger event. Such a comparison may be performed using any suitable technique, including those described above.

In act 230, a checklist is created. The content of the checklist may be based on information inferred from the notification of a trigger event, or on any other available information, which may determine whether a prompt and/or action is to be included in the checklist and the content of one or more prompts and/or actions. The checklist may be created using the checklist template obtained in act 220, and may use some or all of the information in the notification of a trigger event received in act 210 and/or may use information inferred from the notification of a trigger event, as described above. Each prompt and/or action of the checklist may include information that may be used to present the checklist at a terminal device, which may be generated from the checklist template as described above.

A checklist may include additional information, which may or may not be generated from the checklist template. For example, a checklist may include information associated with a particular prompt, such as a textual summary of the prompt (e.g., "Confirm Patient Name") and/or may include information associated with a particular action (e.g., "Patient Name is John Doe"). However, any information, in any suitable form, may be included in a checklist, including text data, image data, audio data and/or a structured document, such as an XML document. Some or all of the information in a checklist (beyond that originating in the checklist template) may be generated from the notification of a trigger event, from an enterprise data base (e.g., a hospital's electronic medical records database) or on any other available information source, including information inferred from the notification of a trigger event, as described above.

The checklist may be created from the checklist template via any suitable technique, which may include combining information from the notification of a trigger event with the checklist template to create the checklist. For example, a checklist template may include a prompt in which a patient's potential allergy to a medication is queried. The notification of a trigger event may include an event data item indicating whether the patient is allergic to the medication, in which case this information may be used to populate part of the checklist (e.g., add instruction to administer a different medication in place of the one to which the patents is allergic).

A non-limiting exemplary technique for creating a checklist from a checklist template is described as follows. A checklist template to be used for a surgery time-out may indicate the following prompts, where actions associated with each prompt are indicated via numerals i, ii, iii, etc.:
  A. Confirm all team members have been introduced and actively participate:
    i. Yes
  B. Surgeon, anesthesia care provider, circulator and scrub tech verbally confirm:
    i. Patient
    ii. Site
    iii. Procedure
  C. Has patient received cardiac clearance for procedure?
    i. Yes
    ii. No
  D. Has intra-operative fasting glucose monitoring been ordered?
    i. Yes
    ii. No In the present example, a checklist may be generated from the checklist template for a surgery time-out event involving a patient that has no history of heart issues. The patient history may be obtained in any suitable way, including by information included in a notification of a trigger event, by performing a lookup based on information included in a notification of a trigger event, etc., as described above.

In the present example, a checklist for the patient is generated from the checklist template to include the following prompts, where actions for each prompt are indicated via numerals i, ii, iii, etc.:
  A. Confirm all team members have been introduced and actively participate:
    i. Yes
  B. Surgeon, anesthesia care provider, circulator and scrub tech verbally confirm:
    i. Patient
    ii. Site
    iii. Procedure
  D. Has intra-operative fasting glucose monitoring been ordered?
    i. Yes
    ii. No The checklist therefore includes all prompts included in the checklist template except for prompt C. The information that the patient has no history of heart issues was used in the generation of the checklist to remove prompt C from the checklist template as being not applicable to the present use case (i.e., as involving a patient with no history of heart issues). The specific technique used to generate the checklist may be any suitable technique, including those described above.

The above is intended to provide a conceptual example of one technique for generating a checklist from a checklist template, and in general any technique may be used, including those described above. Further, the above representations of a checklist and checklist template are not intended to limit ways in which checklists and checklist templates may be represented by a system, but are provided merely as conceptual descriptions.

When creating a checklist in act 230, the checklist may, or may not, include one or more prompts or actions based on whether information is available to populate the prompt and/or action (e.g. from the notification of a trigger event). For example, a checklist may include a prompt that is populated with information when the information indicated by the prompt or action is available (such as in the above example), and may include the prompt not populated with information when the information is unavailable. A particular prompt or action may also not be included in a checklist based on whether information is available to populate the prompt and/or action. Accordingly, a checklist may be created from a checklist template that indicates whether a particular prompt or action is to be included in the checklist, but the content of the prompt or action, and whether it is present in the checklist, may depend on information provided in the notification of a trigger event and/or on the information that is available.

When creating the checklist, the creation of one prompt or action may affect the creation of subsequent prompts and/or actions in the checklist. For example, a checklist template may create a checklist using a tree-like path structure (algorithm—i.e., logic and flow) such that the creation of one prompt or action in the checklist may occur in one of multiple ways, and the way that is used to create the prompt or action may, at least in part, determine how subsequent prompts and/or actions in the checklist are created. For example, a checklist template may include a prompt in which a patient's gender is queried and a subsequent prompt in which it is queried whether the patient is currently pregnant, conditional on the first answer being that the patient is female. When creating a checklist from this checklist template, the first prompt may be populated to indicate the patient is male, in which case the second prompt may be excluded from the checklist based on the creation of the first prompt (since the second prompt would no longer apply to the patient). More complex configurations of checklist templates may be used, however, and each prompt and/or action in a checklist may depend on any number of other prompts and/or actions in the checklist template, or on any other information included in the checklist template.

In act 240, the checklist is provided to a terminal device. A terminal device may be a personal computer, a dumb terminal, a thin client, a tablet computer, a phone, or any other device capable of receiving data input and presenting data output to a user.

Figure 3:
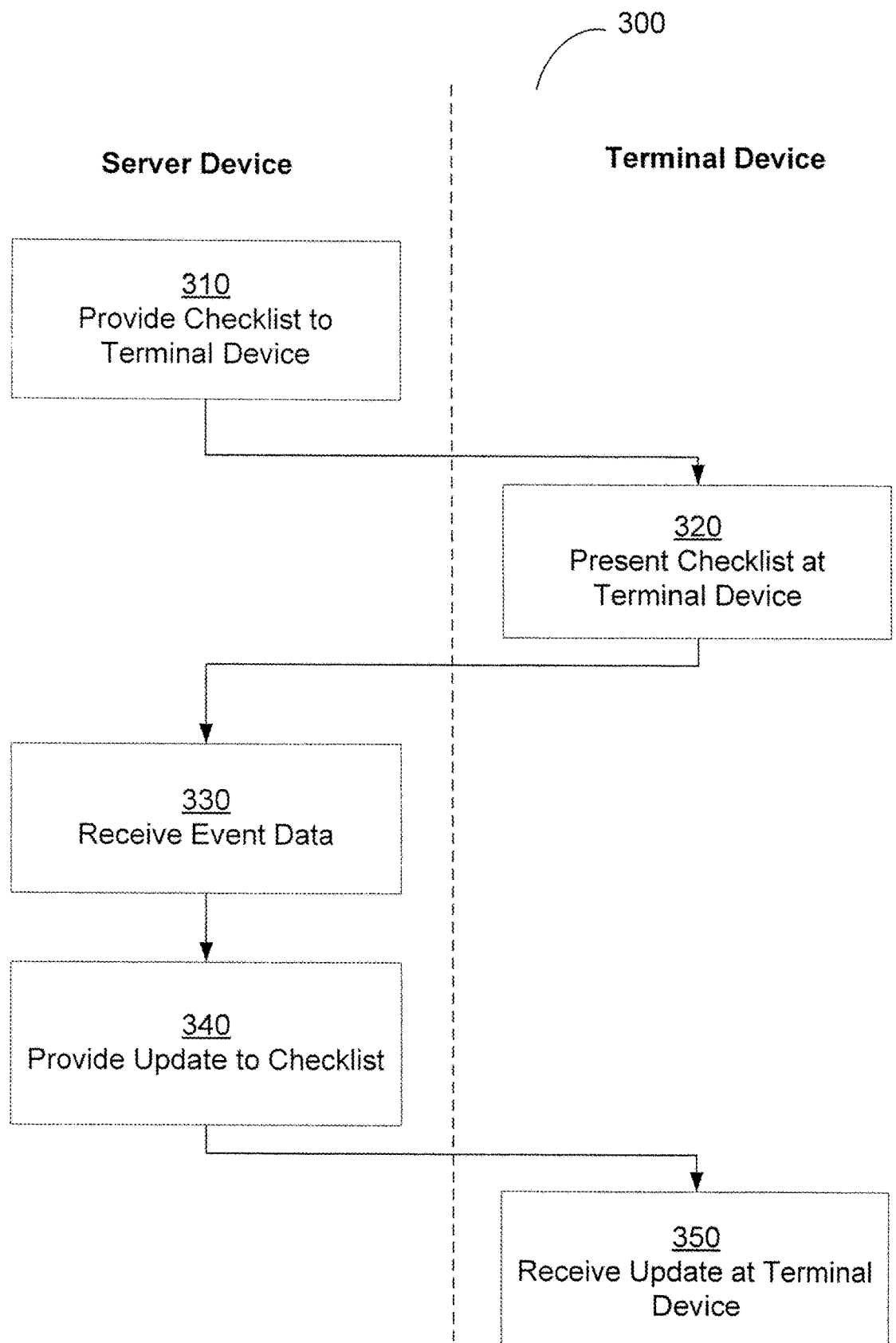
FIG. 3 shows a method of updating an electronic, interactive checklist on a terminal device, according to some embodiments.

FIG. 3 illustrates a method of updating a checklist on a terminal device, according to some embodiments. Method 300 may be performed to provide updates to a checklist in a variety of situations, including, but not limited to, when a terminal device requests an update to a checklist, when new information is available, etc. Method 300 provides an update to a checklist by receiving event data at a server and by providing an update to a checklist at a terminal device based on the event data. The event data may be received from the terminal device to which the update is provided, or may be received from any other suitable device, examples of which are described in further detail below. By providing a server device with up-to-date event data, the accuracy of information in checklists on one or more terminal devices may accordingly be improved.

In act 310, a checklist is provided to a terminal device from a server device. The checklist may be created by any method, including via method 200 shown in FIG. 2, and may be provided from a server device to the terminal device by any method, including wired and wireless communication techniques, and by using any technique(s), including but not limited to TCP/IP, HTTP, Bluetooth™, etc. As described above, the checklist typically includes a sequence of prompts, and each prompt may indicate one or more actions. According to some embodiments, the checklist is a medical checklist that includes prompts and/or actions that relate to one or more medical activities.

A terminal device may be any device capable of receiving data and presenting the data to a user, including but not limited to a personal computer, a dumb terminal, a thin client, a tablet computer, a phone, etc. and may include one or more components for presenting a checklist to a user, such as a display and/or a speaker. A server device may be any device capable of receiving data from at least one data source and of providing data to at least one terminal device, including but not limited to an application server, database server, web server (e.g., an Apache web server), etc. It should be appreciated that the server device may include multiple components that may include, but are not limited to, one or more processors, memory, a database system, etc., which will be described in further detail below. The server device may also comprise multiple computer devices coupled together that appear as a single unified device to other devices.

In act 320, the checklist is presented at the terminal device. The checklist may be presented in any suitable way, including but not limited to display on a screen or monitor, or played through an audio device, such as a speaker or headphones.

In act 330, event data is received by the server device. The event data may indicate any data that is required to be collected or that may alter the users' actions or checklist's content; for example, event data may include one or more medical activities, including but not limited to, a patient entering an operating room, an indication that surgery has begun in an operating room, that anesthesia has been provided to a patient, that a certain time has elapsed, etc. Event data may include a unique identifier that is used to identify the event data, e.g., for logging or reporting purposes, as described above. Event data may include one or more event data items that provide details of the medical activity indicated by the event data. For example, for the event of a patient entering an operating room, the event data may indicate the identification number of the operating room, the name of the patient, the date and time, etc. It should be appreciated that one activity may result in the creation of event data from multiple devices. For example, a patient entering an operating room may be indicated by a location sensor and may also be indicated by a user entering the patient's location on a terminal device.

The event data may be received from a terminal device, or by any other suitable device, including one or more controllers and/or sensors. Examples of suitable devices include, but are not limited to, motion sensors, voice controllers, voice recognition systems, physiological monitors such as anesthetic information monitoring systems (AIMS), real-time location systems, remote input devices, etc. Event data may be received by the server device via any suitable wired or wireless technique, using any suitable protocol, both which may depend on the type of device providing the event data. e.g., a terminal device may connect via a wired TCP/IP connection whereas a real-time location system may communicate via a wireless Bluetooth™ connection.

Event data received by the server device may be used to identify unexpected circumstances, for example, if event data received by the server device contradicts other data available to the server device. In such cases, the server device may provide an indication of the unexpected circumstances, which may be sent to one or more devices with which the server can communicate, such as one or more terminal devices, but may also be displayed as an indication on the server device itself. As an example of the above described technique, event data provided to the server device may indicate a patient's date of birth as 04/29/1972 and the server device may access a stored indication of the patient's date of birth as being 03/29/1972. Since the two indications of the patient's date of birth do not match, the server device may provide an indication of unexpected circumstances. The indication of unexpected circumstances may be provided to one or more terminal devices, and/or may be provided to a device from which the event data was received.

In act 340, an update is provided to a checklist. The server device may perform processing and/or may communicate with another device, such as a database server, to determine the update to be provided. In some cases, it may be determined that no updates are to be provided. In other cases, the update may be provided to some or all of the terminal devices that the server is connected to.

The update may include one or more additions, modifications or deletions to be applied to one or more prompts and/or actions of a checklist. For example, the update may be created as a result of a patient being administered a particular drug, and may include information on how to modify a checklist to indicate that the drug was, in fact, administered (and may also include information such as the name of the drug and the time it was administered).

Checklists and terminal devices to which the update is to be sent may be determined based on a log of checklists that have been provided, and to which terminal devices they have been provided. For example, a database or shared memory accessible to the server device may be searched to determine which checklists, if any, are to be updated, and if so to which terminal devices the checklists were provided. According to some embodiments, the terminal devices are thin clients and the checklists are stored on (or accessible to) the server device such that the contents of the checklists are provided to the terminals via a network connection. Updates to the checklists may then be applied within the server device, which effects an update of the content shown at the terminal device. An example of this type of configuration is described in greater detail below.

Figure 4:
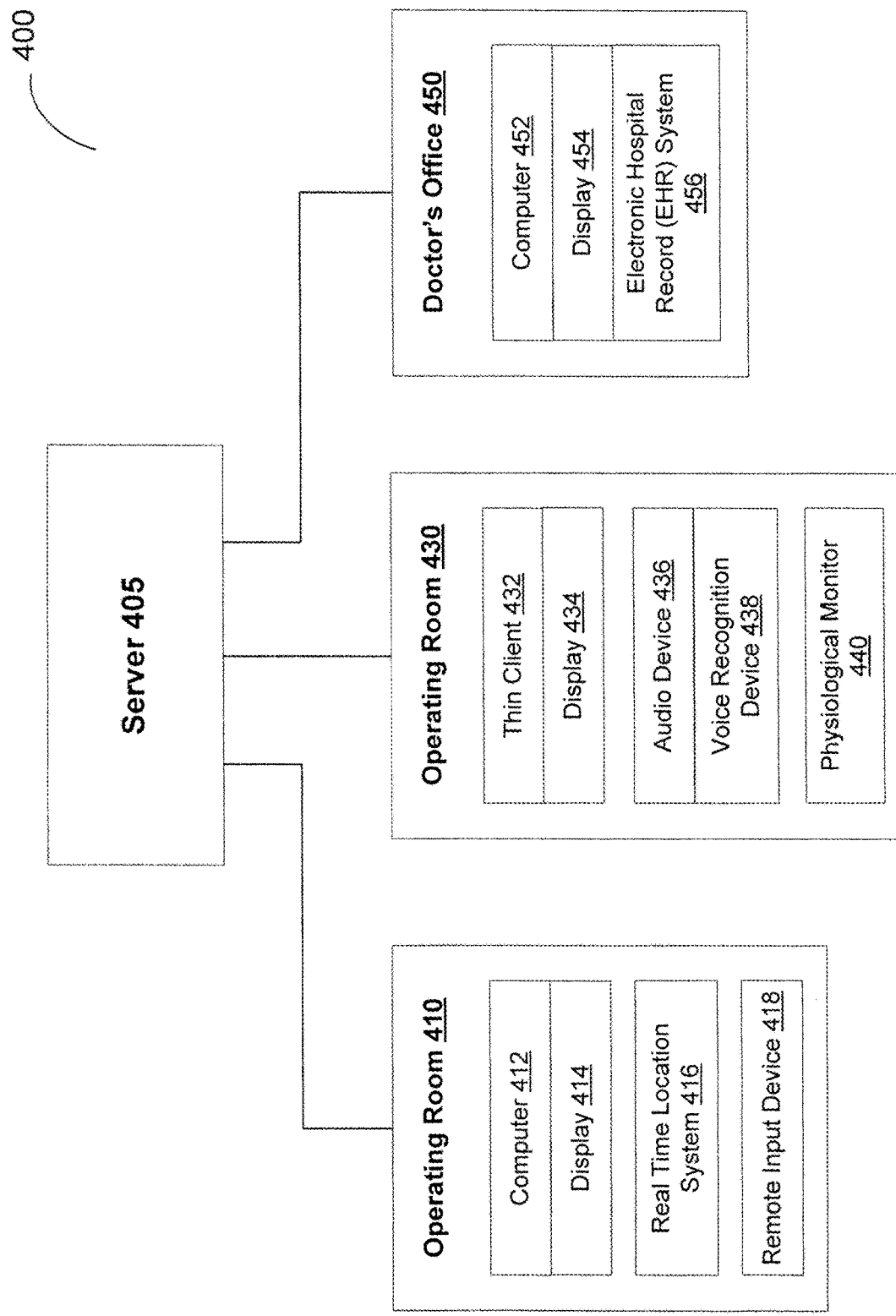
FIG. 4 is a schematic view of an exemplary implementation of an operating room checklist system, in accordance with some embodiments.

FIG. 4 depicts a schematic view of an exemplary implementation of an operating room checklist system, in accordance with some embodiments. In this example, system 400 comprises server 405 which is operatively connected to devices 412, 414, 416 and 418 in operating room 410, to devices 432, 434, 436, 438 and 440 in operating room 430, and to devices 452, 454 and 456 in doctor's office 450. In general, the server may be connected (via appropriate interfaces and communications networks or links) to any number of devices in any number of locations. A location may contain other types of devices not shown in FIG. 4. A location may contain a single device and may contain multiple devices of the same or different types (e.g., two physiological monitors).

Operating room 410 may include computer 412. As a non-limiting example, computer 412 may be a personal computer running an operating system such as a Microsoft Windows™ operating system. In such cases, computer 412 may be connected to server 405 via a wired or wireless (or hybrid) connection, the choice of which may depend on the architecture of operating room 410 (e.g., whether a wired connection is physically available in the room, or whether computer 412 is located close enough to a wired connection to be conveniently connected to it via a wired connection). Computer 412 typically includes one or more input devices, such as a keyboard, mouse, trackball, voice controller, etc. Computer 412 is coupled to display 414, which may be any device capable of displaying an image, including, but not limited to a monitor, television, projector, tablet computer, other handheld display device, etc.

Operating room 410 may include a real-time location system (RTLS) 416, which may be used to track the location of one or more patients, doctors, nurses, etc. Real-time location system 416 may use any suitable technology, including, but not limited to, radio-frequency identification (RFID), Bluetooth™, Wireless Local Area Network, GPS-based mobile phone tracking, etc. and may provide data to server 405 indicating the presence of one or more individuals in operating room 410. The use of a real-time location system may allow server 405 to record the date and time that particular individuals entered and/or left operating room 410. Whether an individual is tracked may depend in part on the technology being used (e.g., using mobile phone tracking it may be difficult to track a patient not carrying a mobile phone, though in some cases a hospital may give a patient a phone or tracking beacon upon admission), and may also depend on whether the system has been configured to track an individual (e.g., whether the individual is wearing an RFID device, whether a gurney or wheelchair carrying the patient is equipped with an appropriate device, whether server 405 is configured to monitor the location of the individual, etc.)

Server 405 may take further action based on data provided by real-time location system 416. For example, an update to one or more checklists may be provided, as described above. Server 405 may analyze the data provided by real-time location system 416 to determine whether to take action based on the data. Such analysis may depend, at least in part, on the role of the individual at the hospital (e.g., if he or she is a patient, doctor, nurse, anesthetist, etc.), and/or whether the individual is associated with the location of the real-time location system (e.g., the anesthetist on record is expected to anaesthetize a patient in operating room 410 at approximately the current date and time).

Operating room 410 may include one or more remote input device 418, each of which may comprise one or more buttons and may be used to respond to one or more prompts of a checklist. Such a checklist may be displayed on display 414, the content of which may be generated by computer 412, which may have received checklist data from server 405. Remote input device 418 may comprise any number of buttons, and may be configured to allow a user to provide responses to checklist actions. According to some embodiments, remote input device 418 comprises five buttons: up, down, left, right and enter, which allow navigation of a cursor on a display to select a response to a checklist prompt. Other possible buttons may include, but are not limited to, a 'back' button (e.g., to return to the previous prompt), 'yes,' 'no,' 'n/a,' (e.g., for providing quick responses to simple questions), etc. A remote input device may also include controls with a range of settings, for example a slider to indicate a range of input values, or a trackball or joystick. Remote input devices may take various forms, including pendants worn around a user's arm or neck, devices attached to a wheelchair, gurney, etc. that move with the patient, a handheld device like a cell phone in terms of form factor, a clip-on device, etc. Rather than, or in addition to, having a button for input, a remote input device may be voice controlled.

Preferably such a remote input unit is assigned a unique identification and that device identification is associated, in a database, with a user to whom the device is assigned. Then, all input from the remote input device can be traced to a specific user to whom the input may be attributed, in addition to being date stamped.

Real-time location system 416 and remote input device 418 may communicate with server 405 directly (e.g. via a wired or wireless connection), and/or may communicate with one or more other devices, such as computer 412, which may provide data from the real-time location system and/or remote input device to server 405. In the latter case, computer 412 may provide a more reliable and lower latency link from the sensor or controller device to the server 405 (e.g., remote input device 418 may transmit data to server 405 quicker via computer 412 than by providing a direct wireless signal to server 405). Communicating with server 405 via computer 412 may also increase the practicality of a particular configuration of devices in an operating room. Real-time location system 416 and remote input device 418 may communicate with computer 412 via any suitable connection, including but not limited to Bluetooth™, infrared, radio, etc.

Operating room 430 includes thin client 432, which may provide a front end graphical interface to a user via display 434. In this example, server 405 stores data, such as one or more checklists, for the system in operating room 430, and thin client 432 provides an indication of processing performed on server 405. Thin client 432 is coupled to display 434, which may be any device capable of displaying an image, including, but not limited to a monitor, television, projector, etc. and which may display data provided from server 405 to thin client 432.

Audio device 436 may be coupled to thin client 432 via a wired or wireless connection. As non-limiting examples, audio device 436 may be a microphone plugged into thin client 432 or may be a microphone wirelessly connected to thin client 432 (e.g., a wireless headset microphone). In the example of FIG. 4, audio device 436 is coupled to voice recognition device 438, which may comprise any system capable of converting speech to text, such as an automated speech recognition (ASR) system. Audio device 436 and voice recognition device 438 may allow a user to provide speech input, which may be a command, a response to a question or query, or may itself be a question or query. The output of voice recognition system 438 may be provided to server 405 in response to a prompt of a checklist, allowing a user to provide speech to audio device 436 to respond to a prompt of a checklist. It should be appreciated that voice recognition device 438 could also be located within server 405, such that audio device 436 would provide sound recordings to server 405 that are converted to text by the voice recognition device on the server. Voice recognition device 438 and audio device 436 may be incorporated into a single device, such as a handheld device capable of outputting and receiving audio and transmitting converted speech to text to server 405. Any suitable device could be used in this configuration including, but not limited to, a mobile phone.

Operating room 430 may include physiological monitor 440, which may provide physiological data on a patient, to server 405. Non-limiting examples of physiological monitors include a blood pressure monitor, an electrocardiogram, an anesthesia monitor, a blood-oxygen monitor, a thermometer, and an electroencephalograph, but may include any type of medical monitor capable of measuring bodily parameters of a patient. Physiological monitor 440 may allow the presence and/or status of a patient to be provided to server 405, which may, based on this information, create a checklist, provide a checklist to thin client 432 and/or update a checklist being displayed on display 434. Physiological monitor 440 may be coupled to thin client 432, providing a wired connection from physiological monitor 440 to server 405, or may communicate wirelessly with thin client 432 and/or server 405.

Doctor's Office 450 may include computer 452 coupled to display 454, in addition to electronic hospital record (EHR) system 456. Electronic hospital record system 456, also known as an electronic health record system, provides for a user to view and modify patient records, for example via a graphical user interface viewed on display 454. Modifications to a patient's electronic patient record via EHR system 456 may be provided to server 405, which may, based on the modifications, create a checklist, provide a checklist to a terminal device, such as computer 452, and/or update a checklist on a terminal device, such as computer 452. As described above, event data provided by a device, such as EHR system 456 may result in an update to one or more checklists. The checklist that is updated may be any checklist on any device, such as a checklist on computer 412 that is displayed on display 414. For example, a doctor in doctor's office 450 may update a patient's medical record to indicate an allergy to a particular drug. Server 405 may then provide an update to a checklist on computer 412 to indicate the patient's allergy, which may aid hospital staff in operating room 410 when providing responses to the checklist.

It should be appreciated that system 400 is illustrated as including a number of exemplary devices, configurations, etc. but than any given system need not include each of these devices, although a given system might. For example, a system may include a server and a plurality of computers and nothing more, or may include a server, a plurality of thin clients and a plurality of remote input devices. In this respect, a system as illustrated in FIG. 4 may include any number of devices of any types, each configured and coupled to other devices in the system in any number of ways. Furthermore, each device may communicate with any other device in the system, including the server, via any suitable type of wired or wireless connection or protocol, examples of which are provided above.

Figure 5:
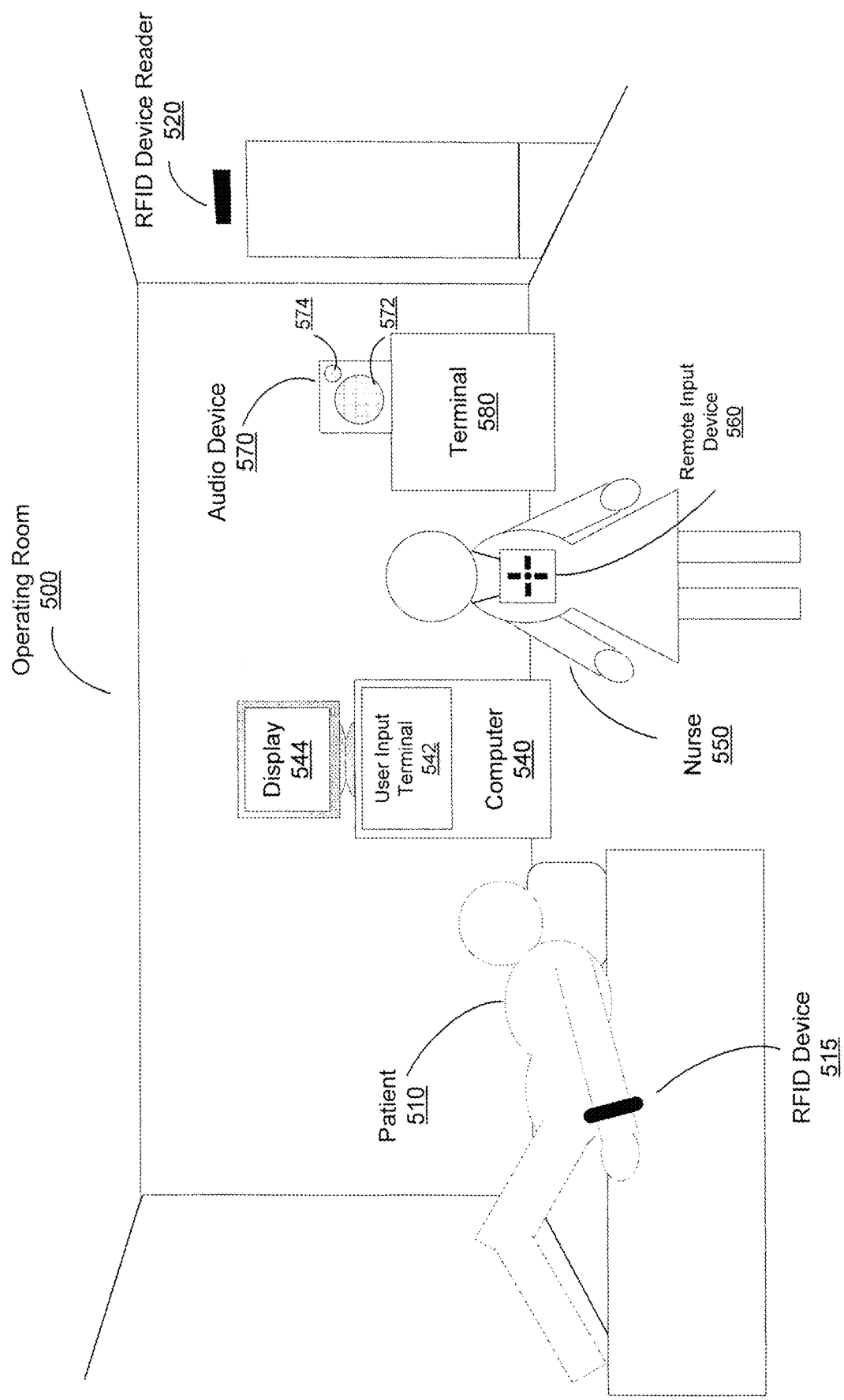
FIG. 5 is a perspective view of an exemplary operating room, suitable for practicing some embodiments described herein.

FIG. 5 illustrates a perspective view of an exemplary operating room, suitable for practicing some embodiments described herein. Operating room 500 includes patient 510 and RFID device 515 attached to the patient's arm. RFID device 515 is configured to provide the location of patient 510 when in proximity of a suitable RFID device reader 520. According to some embodiments, RFID device reader 520 may be configured to communicate wirelessly with a server device to indicate that patient 510 has entered operating room 500. Such an indication may be based upon communication between RFID device 515 and RFID device reader 520.

Operating room 500 also may include computer 540, which includes user input terminal 542 and is coupled to display 544. According to some embodiments, computer 540 may receive a checklist from a server and display checklist prompts and related information on display 544. Such a checklist display may be provided by a server in response to one or more notifications generated by devices in operating room 500, such as by RFID device reader 520 indicating that patient 510 has entered the operating room. As described above, however, any number of devices, both in operating room 500 and elsewhere, may provide a notification to a server that results in the providing of a checklist from a server to computer 540.

Operating room 500 includes remote input device 560 worn around the neck of nurse 550, which may be used to provide responses to one or more prompts of a checklist, for example a checklist being shown on display 544. Remote input device 560 may communicate with computer 540, and may do so via any suitable technique including, but not limited to, infrared, radio, Bluetooth™, etc. In the example of FIG. 5, remote input device 560 is worn by nurse 550, though an input device such as remote input device 560 may in general be worn by any suitable user who may interact with the checklist system (e.g., nurse, anesthesiologist, surgeon, hospital staff, etc.). Providing an input device, such as remote input device 560, in a wearable configuration may provide a convenient way for a user to provide input to a terminal device (e.g., computer 540) and may additionally allow the user to move between locations and provide input to one or more terminal devices using the same wearable input device, at each location.

Operating room 500 includes audio device 570, which may include speaker 572 and microphone 574. Audio device 570 may provide information from one or more prompts of a checklist, for example a checklist displayed on display 544. A checklist may be presented using speaker 572, which may occur simultaneously with the presentation of the checklist on display 544.

Microphone 574 may be used to provide responses to one or more prompts of a checklist, for example a checklist shown on display 544. Audio data from microphone 574 may be sent to a server, and/or may be processed to provide supplemental data and/or converted to a different form (e.g. via a speech-to-text or automated speech recognition system) before being sent to the server. Such processing may occur at any suitable location, including at audio device 570, at computer 540, at a server, etc. Event data received at a server that was determined from audio data obtained by microphone 574 may be processed at one or more locations, and may be communicated one or more times between suitable devices before arriving at the server. In addition, any suitable device may supplement or modify the data before communicating it to another device.

The following scenario is provided as an exemplary embodiment of the above techniques: microphone 574 may capture audio data to which audio device 570 performs audio processing, for example, to remove background noise, perform compression, etc. The processed audio may be wirelessly communicated to a computer 540, which may convert the processed audio to text via an automatic speech recognition system. Computer 540 may then communicate the text in addition to the current date and time and the identification number of operating room 500 to a server as event data using a wired connection.

In the example of FIG. 5, RFID device 515, RFID device reader 520, computer 540, remote input device 560 and/or audio device 570 may communicate with a server, for example to provide event data or notification of a trigger event, and may do so in any number of ways. In addition, each of the above devices may communicate with any of the other devices for any suitable reason, some of which are described above. Devices, including those described above and any number of server devices, may communicate using wired or wireless communication, and using any technique, including but not limited to Ethernet, IEEE 802.11, TCP/IP, IPsec, HTTP, SSH, LDAP, Remote Desktop Services, etc.

It should be appreciated that any number of the devices illustrated in FIG. 5 may be used in any other embodiment, for example by splitting or combining the functionality of the devices described into more or fewer devices, respectively. For example, remote input device 560 and audio device 570 may be combined into a single device capable of providing responses to a checklist in the same manner as remote input device 560, and capable of providing the audio presentation and audio capture functions of speaker 572 and microphone 574 of audio device 570, respectively. Such a combined device may be presented via an application on a mobile phone, for example, although any suitable way to combine two or more functions of two or more devices may be used.

It should be appreciated that operating room 500 is illustrated as including a number of exemplary devices, configurations, etc. but than any given operating room need not include each of these devices, although a given system might. For example, an operating room may include a plurality of computers coupled to displays and nothing more, or may include a thin client, a display and a remote input device. In this respect, an operating room as illustrated in FIG. 5 may include any number of devices of any types, each configured and coupled to other devices in the system in any number of ways. Furthermore, each device may communicate with any other device in the system, including the server, via any suitable type of wired or wireless connection or protocol, examples of which are provided above.

Figure 6A:
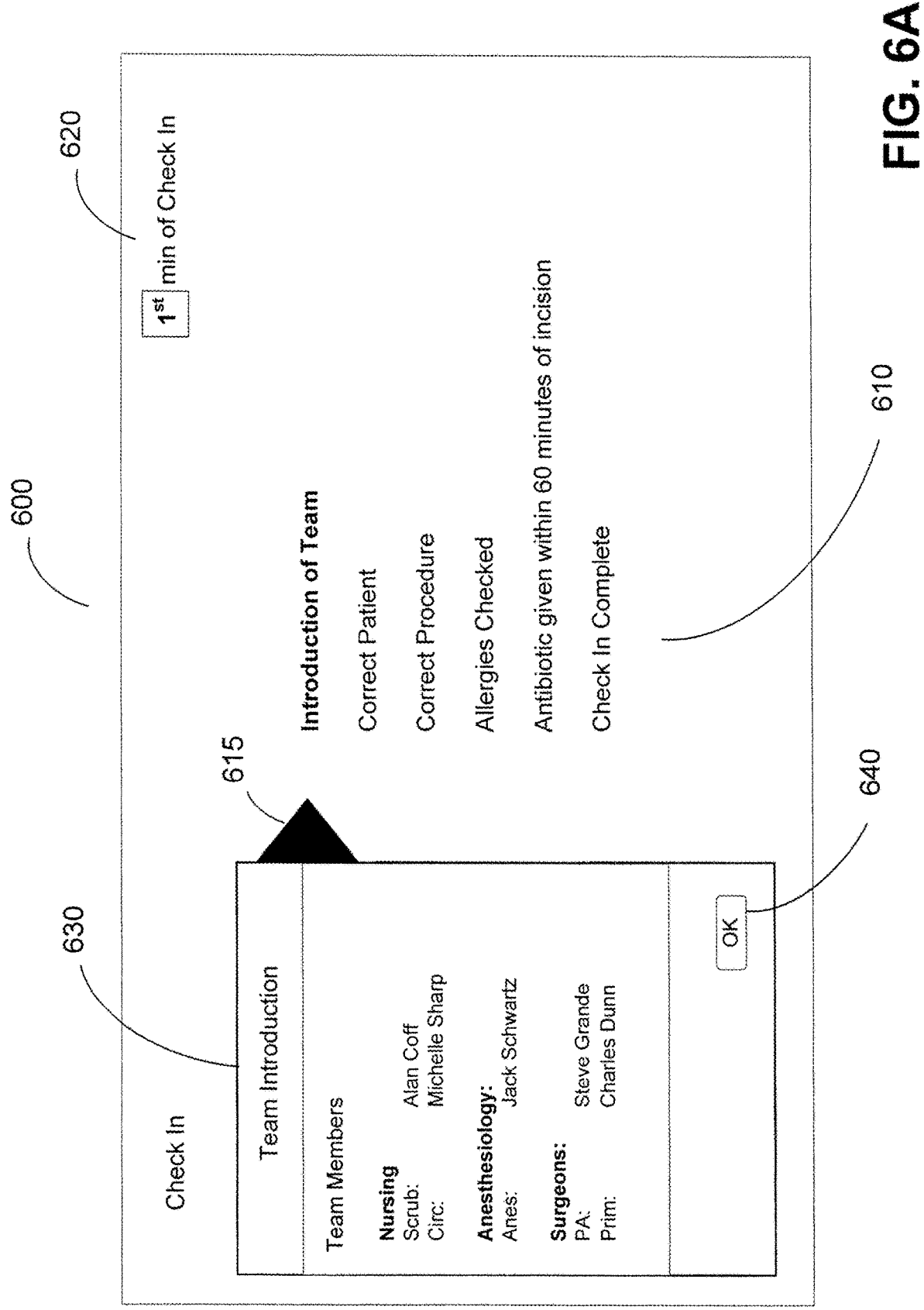
FIG. 6A illustrates a first step of an exemplary checklist, in accordance with some embodiments.

FIGS. 6A-6C illustrate graphical representations of three prompts of an exemplary checklist, in accordance with some embodiments. The graphical representations shown in FIGS. 6A-6C may, for example, be displayed via a terminal device coupled to a display, as described above. In the example of FIGS. 6A-6C, a Check In checklist is represented, which may be used, for example, immediately prior to beginning a surgical procedure. FIGS. 6A-6C represent three prompts in the operation of the checklist, although the Check In checklist depicted may, in general, include more or fewer prompts than those shown, and may or may not appear in the order depicted. Not all prompts in the exemplary checklist are fully depicted, as FIGS. 6A-6C represent three of the prompts in the exemplary checklist.

FIG. 6A illustrates a first step of an exemplary checklist, in accordance with some embodiments. Graphical checklist representation 600 represents each prompt of the checklist as an item in area 610. For example, each prompt may be represented by a summary providing a description of the prompt, which may be provided on separate lines of the graphical representation. However, an indication of a prompt in the current checklist may be represented using any technique, including as icons or as other graphical representations. Furthermore, not all prompts in the checklist may be indicated by any means, or may not all be shown in the graphical representation at the same time (e.g., some prompts may be viewable by use of a scrollbar, or may appear in expandable and/or collapsible sections that may show and/or hide some prompts), as the aspects of the invention are not limited in this respect. The currently active prompt in the checklist may be indicated using any technique, such as by adding a graphical marker, such as graphical marker 615, and/or by highlighting the indication of the prompt, such as by bolding the summary of the prompt as shown in FIG. 6A.

According to some embodiments, graphical checklist representation 600 includes an indication of the length of time for which the checklist has been shown. In the example of FIG. 6A, timing indicator 620 is displayed, indicating the number of minutes since the checklist represented by graphical checklist representation 600 began (e.g., the amount of time since the first prompt in the sequence of prompts of the checklist was graphically displayed). However, an indication of the length of time for which the checklist has been represented may be indicated using any technique, including as a timer showing minutes and seconds, as an image of a clock face, etc. The indication of the length of time for which the checklist has been represented may also include an indication of the type of checklist shown. In the example of FIG. 6A, timing indicator 602 indicates that the checklist shown is a "Check In" checklist.

Graphical checklist representation 600 includes information panel 630, which may be used to provide information and/or to request information from a user, for example, to obtain input in response to a prompt of the checklist. In the example of FIG. 6A, information on a surgical team is shown, which may be information included in the current prompt of the checklist. For example, the checklist may include a prompt that includes a summary of the prompt (e.g., "Introduction of Team") and may include information associated with the prompt (e.g., the content of information panel 630). However, as described above, a prompt may include any number of items of information, some or all of which may be represented in graphical checklist representation 600.

According to some embodiments, some or all of the information displayed in information panel 630 may be obtained from a server and/or from any other suitable device. For example, the list of team members shown in information panel 630 in FIG. 6A may be obtained from a server, for example via method 300 shown in FIG. 3. As one non-limiting example, a terminal device may provide event data indicating that a prompt in the checklist is to be displayed, and a server may respond with an update providing some or all of the information shown in information panel 630. As a further non-limiting example, one or more of the surgical staff present in an operating room may be wearing or holding RFID devices that are recognized by an RFID device reader in the operating room, from which data may be communicated to a server. When the prompt of the checklist is displayed, the server may provide some or all of the information shown in information panel 630 based on the information provided by the RFID device reader. The above are provided merely as exemplary techniques, and any suitable technique for generating content for information panel 630 may be used, including all of the techniques described herein.

According to some embodiments, the information displayed in information panel 630 may indicate unexpected circumstances, as described above. For example, a server may receive an indication of hospital staff that are present in an operating room, which may occur by identifying the hospital staff using one or more RFID device readers. In addition, the server may store a schedule indicating the hospital staff that are expected to be present during a surgery which is to take place in the operating room. If the expected list of hospital staff does not match the indication of the hospital staff present, this unexpected circumstance may be indicated in graphical checklist representation 600, such as in information panel 630. However, any technique for identifying discrepancies between expected and presented data may be used, including those described above.

According to some embodiments, graphical checklist representation 600 may include an indication of one or more actions, such as action button 640. An indication of one or more actions may present information and/or may provide an interface element which may allow a user to provide information in response to a prompt of the checklist. Any number of actions may be represented in graphical checklist representation 600, and may be represented in any suitable way, including as a button, radio button, drop-down list, combobox, check box, datagrid, cycle button, text box, etc. wherein representation of an action may present information and/or may allow a user to provide information. A given action may also be represented in more than one way, for example by both a drop-down list and a text box for one action, where a user may provide information via the dropdown list and/or the text box, either/both of which may provide a response to the same prompt of a checklist.

In the example of FIG. 6A, a single action of the prompt represented by graphical checklist representation 600 is shown as action button 640. As described above, a user may provide a response to the prompt via a number of techniques, such as by pushing a button on a remote or by providing voice commands. In the example of FIG. 6A, a user may provide a response to the prompt represented by graphical checklist representation 600 by pushing a button marked "OK", or by speaking the word "OK" into a microphone (which could be part of a remote input device, for example remote input device 560 shown in FIG. 5), although any other suitable techniques may be used, some of which are described above.

FIG. 6B illustrates a second step of an exemplary checklist, in accordance with some embodiments. Graphical checklist representation 650 shows a prompt that is part of the same checklist as represented by graphical checklist representation 600 in FIG. 6A, but represents a state in which the currently active prompt is different than the active prompt shown in FIG. 6A. According to some embodiments, graphical checklist representation 650 may provide an indication that previous prompts were provided with input. In the example of FIG. 6B, graphical checklist representation 650 includes indicator 660, which may be used to graphically represent that a prompt was provided with input. For example, in the example of FIG. 6A, a user may provide input in response to the prompt represented by graphical checklist representation 600 by pushing a button on a remote input device, as described above. Subsequently, graphical checklist representation 650 may be displayed, and may indicate that input was provided to the prompt represented by graphical checklist representation 600 by displaying indicator 660 next to the summary of the prompt represented by graphical checklist representation 600. However, an indication of a prompt having received input in a current checklist may be represented using any technique, including as icons, colored text, or as other graphical representations.

In the example of FIG. 6B, the prompt represented by graphical checklist representation 650 includes an action indicating that a patient's allergies to medication may be checked, which is indicated by the content of information panel 670. According to some embodiments, the action is represented by action indicator 675 which includes action cycle buttons 676 and 677 which may be used to cycle to the previous and next responses to the prompt, respectively. For example, the prompt may include "Yes," "No," and "N/A" as possible responses to the prompt represented by graphical checklist representation 650, although any responses, and any number of responses, may be included in the prompt. Action cycle buttons 676 and 677 may be used to change the currently selected response to the next possible response, which may be configured to loop through the selections (so that selecting either action cycle button repeatedly will endlessly loop through the selections) or to cycle though a list until the start or end of the list is reached (at which point only one action cycle button will allow a user to choose another possible response).

According to some embodiments, the possible responses to the prompt represented by graphical checklist representation 650 may be determined based on one or more notifications of trigger events and/or by event data provided to a server, as described in techniques above. For example, a terminal device may provide event data indicating that a prompt in the checklist is to be displayed, and a server may determine (e.g., based on available data) whether the patient for whom the checklist was generated is allergic to any medications. The server may then respond with an update providing some or all of the information shown in information panel 670. In the example of FIG. 6B, a server may have provided a response indicating that whether the patient is allergic to any medications is unknown, which may occur because this data relating to the patient is not available to the server. Accordingly, in the example of FIG. 6B, a user may provide an indication of whether the patient is allergic to any medications. According to some embodiments, once a user provides such an indication, data from the input may be provided to a server and/or other device and may allow the system to provide this data to another device or to another checklist, at a later point in time (e.g., when the patient is next undergoing surgery).

FIG. 6C illustrates a third step of an exemplary checklist, in accordance with some embodiments. Graphical checklist representation 680 shows a prompt that is part of the same checklist as represented by graphical checklist representation 600 in FIG. 6A and graphical checklist representation 650 in FIG. 6B, but represents a state in which the currently active prompt is different than the active prompts shown in FIG. 6A and FIG. 6B.

According to some embodiments, the prompt represented by graphical checklist representation 680 includes an action indicating that whether a patient was given an antibiotic within the previous 60 minutes may be checked, which is indicated by the content of information panel 690. In the example of FIG. 6C, graphical checklist representation 680 indicates that 1 g of the antibiotic Cefazolin was administered to the patient at 07:40. This indication may be determined via any suitable technique, including those described herein. For example, when a server generated the checklist of which one prompt is represented by graphical checklist representation 680, the server may have populated the prompt with the information shown in information panel 690. The prompt may have been populated by the server via any suitable technique, including those described herein, such as by having a device provide event data that was stored by the server.

The above description is provided purely to illustrate an example technique for displaying a checklist via a display device. In general, any technique for presenting a checklist to a user may be used, including those techniques described herein.

Figure 7:
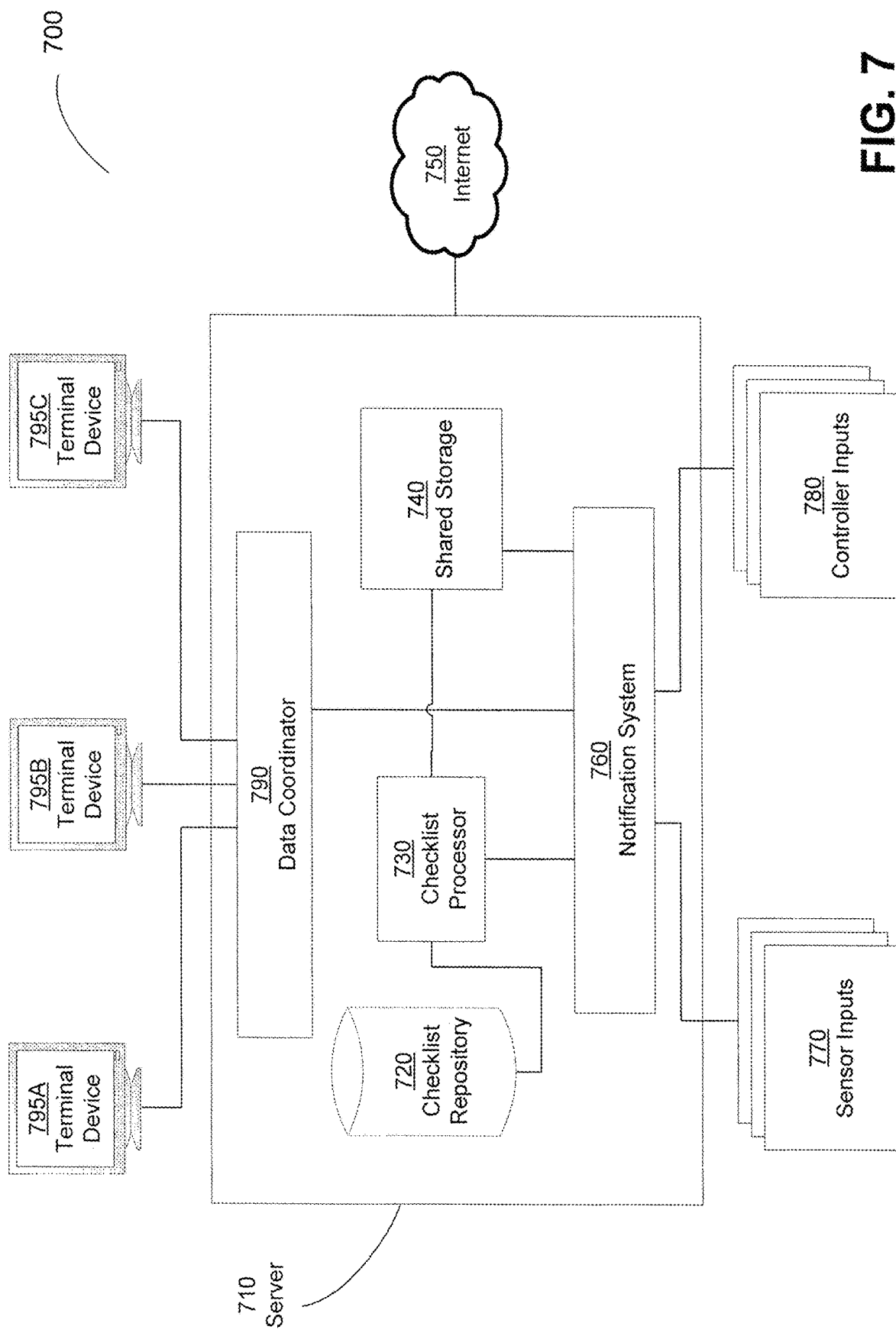
FIG. 7 is a schematic view of a system suitable for practicing some embodiments described herein.

FIG. 7 depicts system 700 suitable for practicing some embodiments described above. In system 700, server 710 is capable of accessing checklist repository 720 including a plurality of checklist templates. Checklist processor 730 may be configured to generate a checklist, for example, using one or more checklist templates in checklist repository 720, and may use one or more techniques to generate the checklist, including but not limited to those described above.

In some embodiments, server 710 includes shared storage 740 which may be used to store data by system 700. Such data may include, but is not limited to checklists, event data (e.g., from one or more terminal devices, sensors and/or controllers), notifications of trigger events (e.g., event identifiers, case identifiers and/or event data items), patient information, electronic hospital records, hospital administration data (e.g., staff records, operating room and equipment manifests), etc. Shared storage 740 may comprise any suitable apparatus, including disk drives and/or memory, etc. and may comprise additional hardware and/or software to allow indexing and/or searching of data, which may include database hardware and/or software. Data in shared storage 740 may be used by checklist processor 730 when generating a checklist. For example, patient information in shared storage 740 may be used to populate a prompt in a checklist being generated for a use case that relates to the patient (e.g., to include the patient's name, age, etc.).

In some embodiments, server 710 is coupled to the Internet 750 to obtain data which may be used to facilitate the generation of a checklist and/or to provide an update to one or more checklists. For example, generating a checklist may include obtaining medical records for a patient that are not present in shared storage 740, but may be available at a system available via the Internet 750 (e.g., via an electronic hospital records system). Data obtained via an Internet query, e.g., via a web service, may be used to generate a checklist and/or to provide an update to a checklist.

In some embodiments, server 710 includes notification system 760 which may receive data from one or more sensor inputs 770 and/or controller inputs 780 and may provide the data to checklist processor 730, to shared storage 740 and/or to data coordinator 790. Sensor inputs 770 may comprise any number or type of sensor devices that may provide data to server 710, including but not limited to physiological sensors, touch sensors, motion sensors, RFID device readers, real-time location systems, etc. For example, a physiological sensor may provide event data to notification system 760, such as by using one or more of the methods or techniques described above. Controller inputs 780 may comprise any number or type of controller devices, including but not limited to remote input devices, voice controllers, scheduling systems, microphones, keypads, touch screens, mice, trackballs, writing pads, computers, timers, etc. For example, a computer may provide a notification of a trigger event to notification system 760, such as by using one or more of the methods or techniques described above. In some embodiments, one or more controllers may be part of server 710, including any of those described above. For example, server 710 may include a scheduling system in order to generate time-driven trigger events without relying on an external controller (e.g., if a procedure, such as a surgery, is scheduled for a specified date and time).

In some embodiments, notification system 760 may include one or more handlers (i.e., computer program code) to perform processing on data received from particular types of sensors and/or controllers. For example, notification system 760 may include a handler for use with data received from physiological sensors, which may perform processing to modify and/or supplement the physiological sensor data before providing the data to checklist processor 730, to shared storage 740 and/or to data coordinator 790. Such processing may be performed for any suitable reason, including but not limited to, for modifying or deleting invalid data, to transform data (e.g., to ensure data values fit into a particular range), etc.

In some embodiments, server 710 includes data coordinator 790, which may be used to provide data to one or more terminal devices 795A-C. A terminal device may be any device capable of presenting data to a user, including but not limited to computers, dumb terminals, thin clients, tablet computers, mobile phones, etc. Any number of any types of terminal devices may communicate with server 710, wherein the communication may be via a wired and/or wireless connection, using any suitable communication technology and/or technique, including but not limited to Ethernet, IEEE 802.11, TCP/IP, IPsec, HTTP, SSH, LDAP, Remote Desktop Services, etc. In some embodiments, data coordinator 790 includes a web server (e.g., an Apache web server) and provides data to one or more terminal devices via Simple Object Access Protocol (SOAP) messages sent over HTTP.

Figure 8:
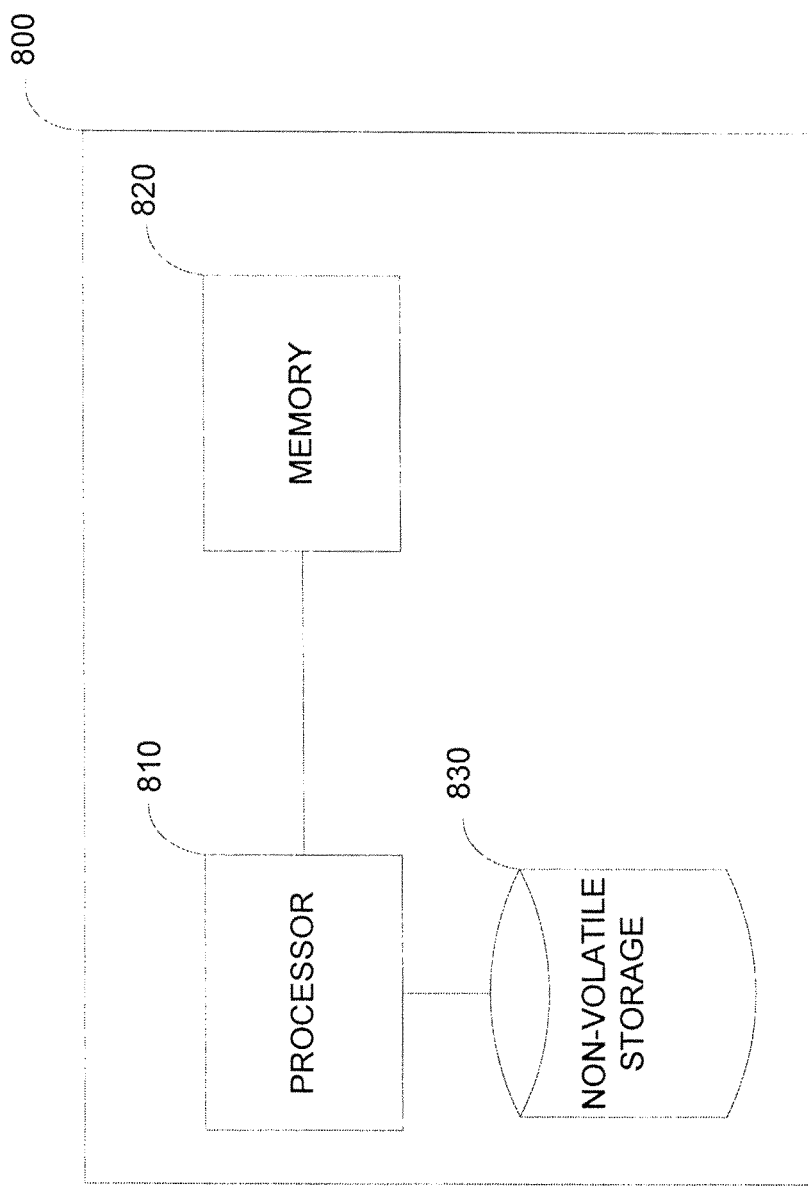
FIG. 8 is a schematic view of a computer system that may be used in connection with any of the embodiments of the invention.

An illustrative implementation of a computer system 800 that may be used in connection with any of the embodiments of the invention described herein is shown in FIG. 8. The computer system 800 may include one or more processors 810 and one or more non-transitory computer-readable storage media (e.g., memory 820 and one or more non-volatile storage media 830). The processor 810 may control writing data to and reading data from the memory 820 and the non-volatile storage device 830 in any suitable manner, as the aspects of the invention described herein are not limited in this respect. To perform any of the functionality described herein, the processor 810 may execute one or more instructions stored in one or more computer-readable storage media (e.g., the memory 820), which may serve as non-transitory computer-readable storage media storing instructions for execution by the processor 810.

In connection with the checklist techniques described herein, one or more checklists or checklist templates may be stored on one or more computer-readable storage media of computer system 800. Any other software, programs or instructions described here may also be stored and executed by computer system 800.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A system for providing and administering medical checklists, the system comprising:
    a plurality of terminal devices including a first terminal device, each terminal device of the plurality of terminal devices configured to:
        display a medical checklist comprising a sequence of prompts, each prompt indicating one or more actions, wherein at least one prompt in the sequence of prompts is displayed only upon completion of a previous prompt in the sequence of prompts;
        receive input from a user in response to a prompt of the sequence of prompts, the input signifying that an action of the one or more actions indicated by the prompt is being performed;
        display, in response to receiving an indication of a discrepancy, information relating to the discrepancy by displaying said information concurrently with display of at least a portion of the medical checklist; and
        update the portion of the medical checklist in response to receiving checklist update data; and
    a server device configured to:
        provide a medical checklist to at least the first terminal device of the plurality of terminal devices;
        receive first event data indicating one or more medical activities, wherein the first event data is not received from the first terminal device;
        compare the received first event data with stored data to determine whether there is a discrepancy between the received first event data and the stored data;
        when it is determined that there is a discrepancy between the received first event data and the stored data, provide said indication of the discrepancy to the first terminal device;
        receive second event data, wherein the second event data is not received from the first terminal device;
        determine whether or not to provide an update to the medical checklist by comparing the received second event data to the stored data; and when it is determined that an update to the medical checklist is to be provided, provide said checklist update data to the first terminal device.

2. The system of claim 1, wherein updating the portion of the medical checklist in response to receiving the checklist update data comprises modifying one or more of the sequence of prompts.

3. The system of claim 1, wherein the first event data is received from one of the plurality of terminal devices other than the first terminal device.

4. The system of claim 1, wherein the first event data is received from a sensor device.

5. The system of claim 1, wherein the first terminal device is further configured to display a graphical representation of the indication of the discrepancy received from the server device.

6. The system of claim 1, wherein at least one terminal device of the plurality of terminal devices is configured to receive input from the user in response to a prompt of the sequence of prompts via one or more controllers.

7. The system of claim 6, wherein at least one controller of the one or more controllers is a motion controller.

8. The system of claim 6, wherein at least one controller of the one or more controllers is a remote input device.

9. The system of claim 6, wherein at least one controller of the one or more controllers is a voice controller.

10. A processor-driven method of providing and administering medical checklists, the method comprising:
at a server device, providing a medical checklist to a terminal device, the medical checklist comprising a sequence of prompts, each prompt indicating one or more actions;
at the terminal device, displaying the medical checklist such that a user is prevented from proceeding from a first prompt in the sequence of prompts to a second, subsequent prompt in the sequence of prompts until the first prompt is completed;
at the server device:
receiving first event data indicating one or more medical activities, wherein the first event data is not received from the terminal device;
comparing the received first event data with stored data to determine whether there is a discrepancy between the received first event data and the stored data; and
when it is determined that there is a discrepancy between the received first event data and the stored data, providing an indication of the discrepancy to the terminal device;
at the terminal device, displaying, in response to receiving the indication of the discrepancy from the server device, information relating to the discrepancy by displaying said information concurrently with display of at least a portion of the medical checklist;
at the server device:
receiving second event data, wherein the second event data is not received from the first terminal device;
determining whether or not to provide an update to the medical checklist by comparing the received second event data to the stored data; and
when it is determined that an update to the medical checklist is to be provided, providing checklist update data to the first terminal device; and
at the terminal device, subsequent to displaying the information relating to the discrepancy, updating the portion of the medical checklist in response to receiving the checklist update data from the server device.

11. The method of claim 10, wherein updating the portion of the medical checklist in response to receiving the checklist update data from the server device comprises modifying one or more of the sequence of prompts.

12. The method of claim 10, wherein the terminal device is a first terminal device of a plurality of terminal devices, and wherein the first event data is received from one of the plurality of terminal devices other than the first terminal device.

13. The method of claim 10, wherein the first event data is received from a sensor device.

14. The method of claim 10, wherein the terminal device is further configured to display a graphical representation of the indication of the discrepancy received from the server device.

15. The method of claim 10, wherein at least one terminal device of the plurality of terminal devices is configured to receive input from the user in response to a prompt of the sequence of prompts via one or more controllers.

16. The method of claim 15, wherein at least one controller of the one or more controllers is a motion controller.

17. The method of claim 15, wherein at least one controller of the one or more controllers is a remote input device.

18. The method of claim 15, wherein at least one controller of the one or more controllers is a voice controller.

19. An operating room including a computer-driven medical checklist presentation and administration system comprising:
one or more sensors configured to provide a notification of a trigger event to a server, the notification being associated with a patient; and
one or more terminal devices, each terminal device configured to:
receive a medical checklist from the server comprising a sequence of prompts, each prompt indicating one or more actions;
display the medical checklist;
receive input from a user in response to a prompt of the sequence of prompts, the input signifying that an action of the one or more actions indicated by the prompt has been performed;
in response to the providing of the notification of the trigger event from the one or more sensors to the server, receive an update to the medical checklist from the server, wherein the update comprises one or more additions, modifications or deletions to be applied to one or more prompts of the sequence of prompts associated with the patient;
apply the received update to the one or more of the sequence of prompts of the medical checklist, thereby producing one or more updated prompts; and
display at least one of the one or more updated prompts.

20. The system of claim 19, wherein at least one sensor of the one or more sensors is a physiological monitor.

21. The system of claim 19, wherein at least one sensor of the one or more sensors is a real-time location system.

22. The system of claim 19, wherein at least one terminal device of the one or more terminal devices is configured to receive input from the user in response to a prompt of the sequence of prompts via one or more controllers.

23. The system of claim 22, wherein at least one controller of the one or more controllers is a motion controller.

24. The system of claim 22, wherein at least one controller of the one or more controllers is a remote input device.

25. The system of claim 19, wherein the sequence of prompts describe a sign-in, time-out or debrief procedure for surgery.

\* \* \* \* \*